(12) United States Patent
Pan et al.

(10) Patent No.: US 6,730,122 B1
(45) Date of Patent: May 4, 2004

(54) PROSTHETIC HEART VALVE WITH INCREASED LUMEN

(75) Inventors: Karl K. Pan, Woodbury, MN (US); James R. Ringdal, Blaine, MN (US); Steven D. Kruse, Bloomington, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/724,618

(22) Filed: Nov. 28, 2000

(51) Int. Cl.$^7$ .................................................. A61F 2/24
(52) U.S. Cl. ........................................ 623/2.33; 623/2.1
(58) Field of Search .................................. 623/2.2–2.35

(56) References Cited

U.S. PATENT DOCUMENTS

| | | | |
|---|---|---|---|
| 3,691,567 A | 9/1972 | Cromie | 3/1 |
| 4,078,268 A | 3/1978 | Possis | 3/1.5 |
| 4,178,639 A | 12/1979 | Bokros | 3/1.5 |
| 4,506,394 A | 3/1985 | Bédard | 3/1.5 |
| 4,535,483 A | 8/1985 | Klawitter et al. | 623/2 |
| 4,597,767 A | 7/1986 | Lenkei | 623/2 |
| 4,601,719 A | 7/1986 | Totten | 623/2 |
| 4,705,516 A | 11/1987 | Barone et al. | 623/2 |
| 4,743,253 A | 5/1988 | Magladry | 623/2 |
| 4,846,830 A | 7/1989 | Knoch et al. | 623/2 |
| 4,888,009 A | 12/1989 | Lederman et al. | 623/2 |
| 4,935,030 A | 6/1990 | Alonso | 623/2 |
| 4,995,881 A | 2/1991 | Knoch et al. | 623/2 |
| 5,035,709 A | 7/1991 | Wieting et al. | 623/2 |
| 5,061,278 A | * 10/1991 | Bicer | 623/2.27 |
| 5,137,532 A | 8/1992 | Bokros et al. | 623/2 |
| 5,314,467 A | 5/1994 | Shu | 623/2 |
| 5,336,259 A | 8/1994 | Waits et al. | 623/2 |
| 5,360,014 A | 11/1994 | Sauter et al. | 128/774 |

(List continued on next page.)

FOREIGN PATENT DOCUMENTS

| | | |
|---|---|---|
| DE | 1 180 087 | 10/1964 |
| EP | 0 465 383 A1 | 6/1991 |
| GB | 2 018 396 | 10/1979 |
| WO | WO 99/37249 | 7/1999 |

OTHER PUBLICATIONS

"The CarboMedics® "Top Hat" Supraannular Prosthesis in the Small Aortic Root," by S. Roedler et al., *J Card Surg*, vol. 10, pp. 198–204 (1995).

"Theory and Problems of Fluid Dynamics, " by W. Hughes et al., *Schaum's Outline Series*, McGraw–Hill Book company, pp. 3–4 and 84 (1967).

"Rationalizing Antithrombotic Management for Patients with Prosthetic Heart Valves," by E. Butchart, *The Journal of Heart Valve Disease*, pp. 106–113, (1995).

"Prosthetic Valves for the Small Aortic Root," by H. Barner et al., *J Card Surg*, vol. 9, pp. 154–157 (1994).

Brochure entitled: "St. Jude Medical Mechanical Heart Valve Hemodynamic Plus Series" (1995).

Baxter, "Edwards–Duromedics™ Bileaflet Valve", pp. 1–7, 1989.

"The St. Jude Medical® Mechanical Heart Valve Hemodynamic Plus (HP) Series", by St. Jude Medical, Inc. St. Paul, Minnesota, 1996.

*Primary Examiner*—Corrine McDermott
*Assistant Examiner*—Thomas C. Barrett
(74) *Attorney, Agent, or Firm*—Altera Law Group, LLC; Hallie A. Finucane (57) ABSTRACT

A prosthetic heart valve for replacing a native heart valve is provided and includes a generally circular heart valve body having an inner wall defining a lumen configured to allow blood flow therethrough. Occluders are configured to rotate about opposed occluder ends between an open position and a closed position. The minor radius arcs cooperate with the occluders to allow the occluders to block blood flow through lumen when in a closed position yet provide an increased lumen when the occluders are in an open position.

18 Claims, 8 Drawing Sheets

U.S. PATENT DOCUMENTS

| | | | |
|---|---|---|---|
| 5,545,216 A | 8/1996 | Bokros et al. | 623/2 |
| 5,562,729 A | 10/1996 | Purdy et al. | 623/2 |
| 5,641,324 A | 6/1997 | Bokros et al. | 623/2 |
| 5,741,328 A | 4/1998 | Reif | 623/2 |
| 5,824,062 A * | 10/1998 | Patke et al. | 623/2.26 |
| 5,908,452 A | 6/1999 | Bokros et al. | 623/2 |
| 5,919,226 A * | 7/1999 | Shu et al. | 623/2.31 |
| 6,007,577 A | 12/1999 | Vanney et al. | 623/2 |
| 6,139,575 A | 10/2000 | Shu et al. | 623/2.12 |

* cited by examiner

PROSTHETIC HEART VALVE WITH INCREASED LUMEN

FIELD OF THE INVENTION

The present invention relates to prosthetic heart valves. More particularly, the invention relates to an increased valve lumen of a prosthetic heart valve to improve hemodynamic performance.

BACKGROUND OF THE INVENTION

Prosthetic heart valves are used as a replacement for natural heart valves of patients. A standard implantable mechanical heart valve typically includes an annular valve housing or body (often called an "orifice") to provide a lumen or passageway therethrough for blood flow. One or more occluders mounted to the valve are movable between an open position, allowing blood flow, and a closed position which blocks blood flow. In many mechanical valves, the occluders are essentially plate-like members called "leaflets." Typical configurations include one, two or three leaflets in the valve body.

There has been an ongoing effort to improve the performance of prosthetic heart valves. One important factor in heart valve performance is the flow characteristics through the valve when the leaflets are in a fully open position. Compared with native valves, mechanical heart valves have flow characteristics with higher peak velocities and greater variation in velocity across the valve, leading to higher shear stresses and a more turbulent flow structure. As a result, prosthetic heart valves have higher energy loss and correspondingly higher pressure differentials across the valve than the native valve. The forward flow characteristics of the valve can be altered by increasing the valve lumen area allowing full alignment of the leaflets with the direction of flow, and improving the shape of the lumen valve among other techniques.

Another problem which may be associated with mechanical heart valves relates to formation of thrombus and thromboembolism. Thrombus and thromboembolism are known complications of mechanical heart valves and can result in serious disability or death. To help prevent these complications, a common treatment involves life-long anticoagulant therapy. However, anticoagulant therapy itself leads to an increased risk of anticoagulant-related hemorrhage.

Factors which influence the risk of thrombus and thromboembolism formation for mechanical heart valve patients include the nonphysiological surfaces and blood flow introduced by mechanical valves. Further, typical mechanical heart valves subject the blood to high shear stress, largely because such valves tend to produce high velocity gradients and turbulent flow structures. High shear stresses are known to activate blood platelets and damage red blood cells. The activated platelets have the potential to be deposited on the valve or downstream from the valve and to aggregate into thrombi. Therefore, valves with mean forward flow velocities and peak shear stresses which are lower than prior art valves would be beneficial to patients.

SUMMARY OF THE INVENTION

A prosthetic heart valve for replacing a native valve in a heart is provided and includes a generally circular heart valve body having an inner wall defining an orifice configured to allow blood flow therethrough. At least one occluder in the orifice is configured to rotate about opposed occluder ends between an open position and a closed position. The occluder is configured to substantially block blood flow through the orifice in the closed position. In one aspect, minor radius arcs are formed in the inner diameter of the heart valve body to receive the minor radius arcs of the occluder. The curved surface with minor radius arcs extends the full length of the orifice to seal the occluders in the closed position and allow the occluders to rotate to a fully open position without interference.

DETAILED DESCRIPTION OF THE PREFERRED EMBODIMENTS

The present invention relates to a mechanical prosthetic heart valve of the type used to replace a native tissue valve of a heart. The present invention provides designs to increase the area of the lumen through the heart valve to provide improved blood flow characteristics and reduced obstruction to such flow.

Typical mechanical heart valves have parallel planar sections on the inner wall of the valve body to carry the pivot mechanisms to allow the occluders to pivot. These are essentially flat sections on the inner diameter of the valve body and tend to reduce the overall lumen area which is available to blood flow. In one embodiment of the present invention, these flat planar sections are replaced with minor radius arcs which increase the lumen area available to blood flow, and minimize flow disturbance through the valve. In other embodiments, a flat section is maintained between the center line of the minor radius arc.

Figure 1:
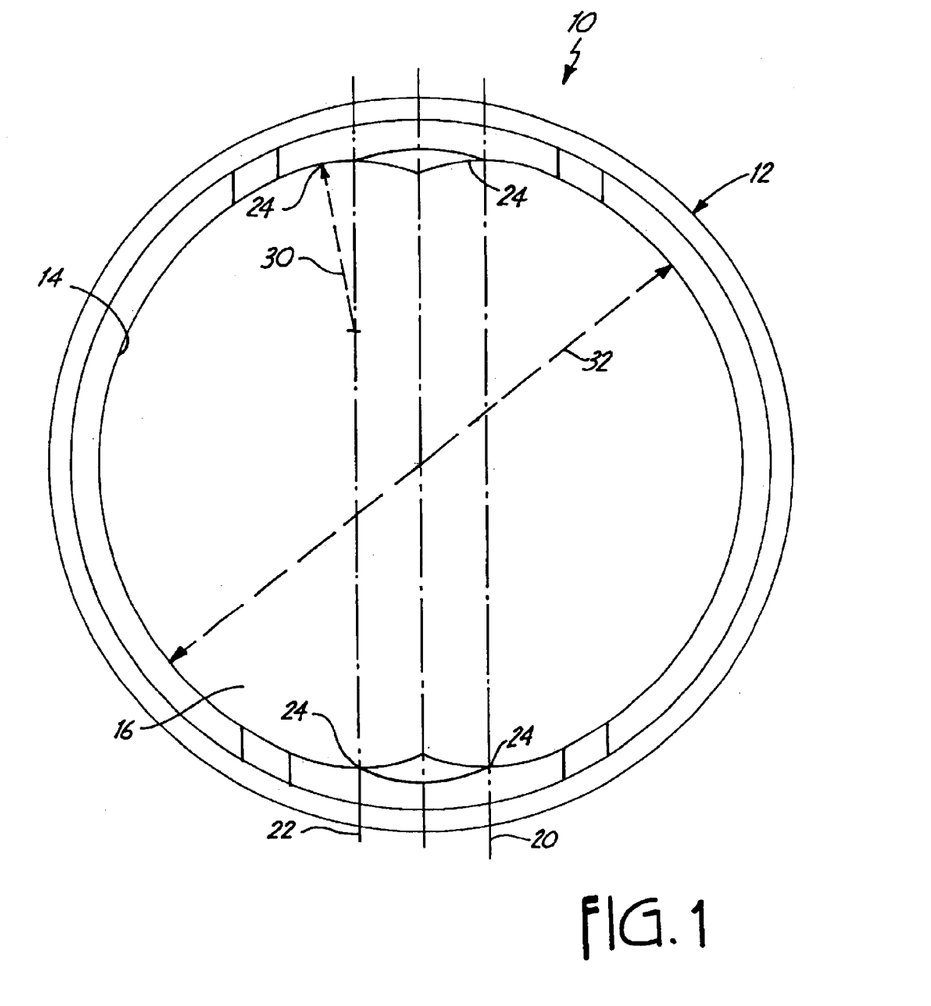
FIG. 1 is a top plan view of a prosthetic heart valve in accordance with one embodiment of the present invention.

FIG. 1 shows one embodiment of the present invention. FIG. 1 is a top plan view of a prosthetic heart valve 10 having an orifice or valve body 12 which includes an inner wall 14 forming a lumen 16 therethrough. Pivot mechanisms 60 (shown in FIG. 3) are positioned on opposite sides of valve body 12 and carry first and second occluders (not shown in FIG. 1) which pivot about axis 20 and axis 22. FIG. 1 illustrates the positioning and configuration of orifice minor radius arcs 24 on valve body 12 relative to axis 20 and axis 22. The minor radius arcs 24 cooperate with the occluders to allow the occluders to block blood flow through lumen 16 when in a closed position yet provide an increased lumen when the occluders are in an open position. In the embodiment illustrated in FIG. 1, a radius 30 of a minor radius arc 24 may be tangent to a major radius 32 of the lumen 16 and has a length which is about one half of the length of major radius 32. In another example embodiment, the radius 30 of minor radius arcs 24 is substantially the same in length as major radius 32 of lumen 16 such that the orifice is completely cylindrical. As illustrated in FIG. 1, the axes 20 and 22 are coincident with the center of the minor radius arcs 24 such that as the occluders rotate about axes 20 and 22 to the closed position, and the minor radius arcs 24 and the minor radius arcs. (see FIG. 4) of the occluders mate.

Figure 2:
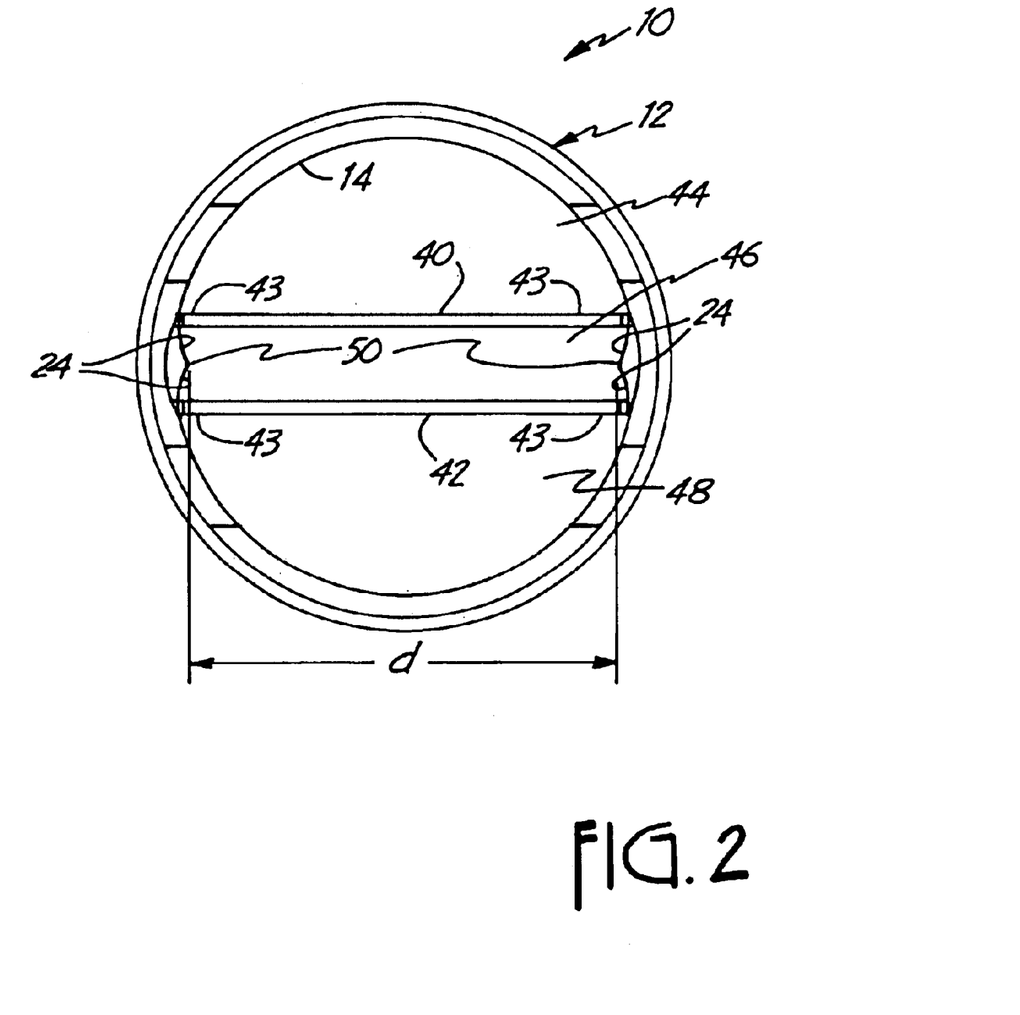
FIG. 2 is a top plan view of the prosthetic heart valve of FIG. 1 showing occluders positioned therein.

FIG. 2 illustrates heart valve prosthesis 10 including occluders 40 and 42 retained by the pivot mechanism. Occluders 40 and 42 have minor radius arcs 43 which mate with valve body minor radius arcs 24. As illustrated in FIG. 2, the areas 44,48 are larger than area 46. In all configurations, the spacing between axes can be adjusted to optimize uniform flow through the valve. As the spacing between axes increases, the area distribution between areas 44, 46 and 48 becomes more uniform,. At an axes spacing of about 28% of the lumen diameter, the three areas 44, 46 and 48 will be approximately equal. This uniform distribution between, the three areas will tend to more evenly distribute flow through the lumen, resulting in a more uniform velocity profile through the valve. The space between axes 20,22 can be optimized such that the distance between them is between about 10% and about 40% of the diameter of the lumen and preferably between about 15% and about 25%.

Figure 3:
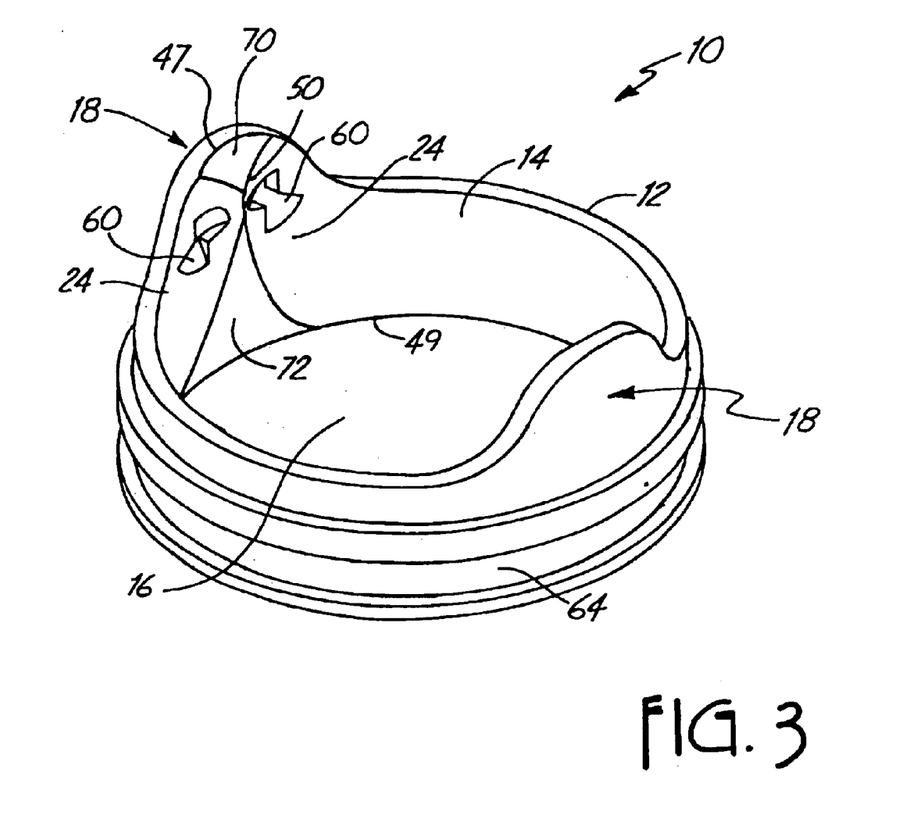
FIG. 3 is a perspective view of the prosthetic heart valve of FIG. 1.

FIG. 3 is a perspective view of valve 10 and shows minor radius arcs 24 in greater detail. Pivot mechanisms 60 are shown in minor radius arcs 24 and receive occluder ends 45 (FIG. 4) from occluders 40 and 42 to provide a pivot mechanism. However, any type of pivot mechanism can be used including other configurations or configurations in which protrusions are provided on the inner wall 14 of body 12. Ends 45 can be concave or convex to provide a protruding or a receiving geometry, and peaks 50 can be on the leaflet.

FIG. 3 also shows outside diameter recess 64 which can be used to attach an attachment mechanism such as a suture cuff. Of course, any attachment mechanism can be used. FIG. 3 also shows tapered regions 70 and 72 proximate minor radius arcs 24. The tapered regions 70 and 72 at the inlet and outlet of valve 10 provide a transition from the peak extensions 50 of minor radius arcs 24 to the full diameter of lumen 16. Regions 70,72 taper outwardly from the peak extension 50 to the inflow edge 47 and outflow edges. This configuration is such that the inlet and outlet of the valve 10 may be substantially circular.

Figure 5:
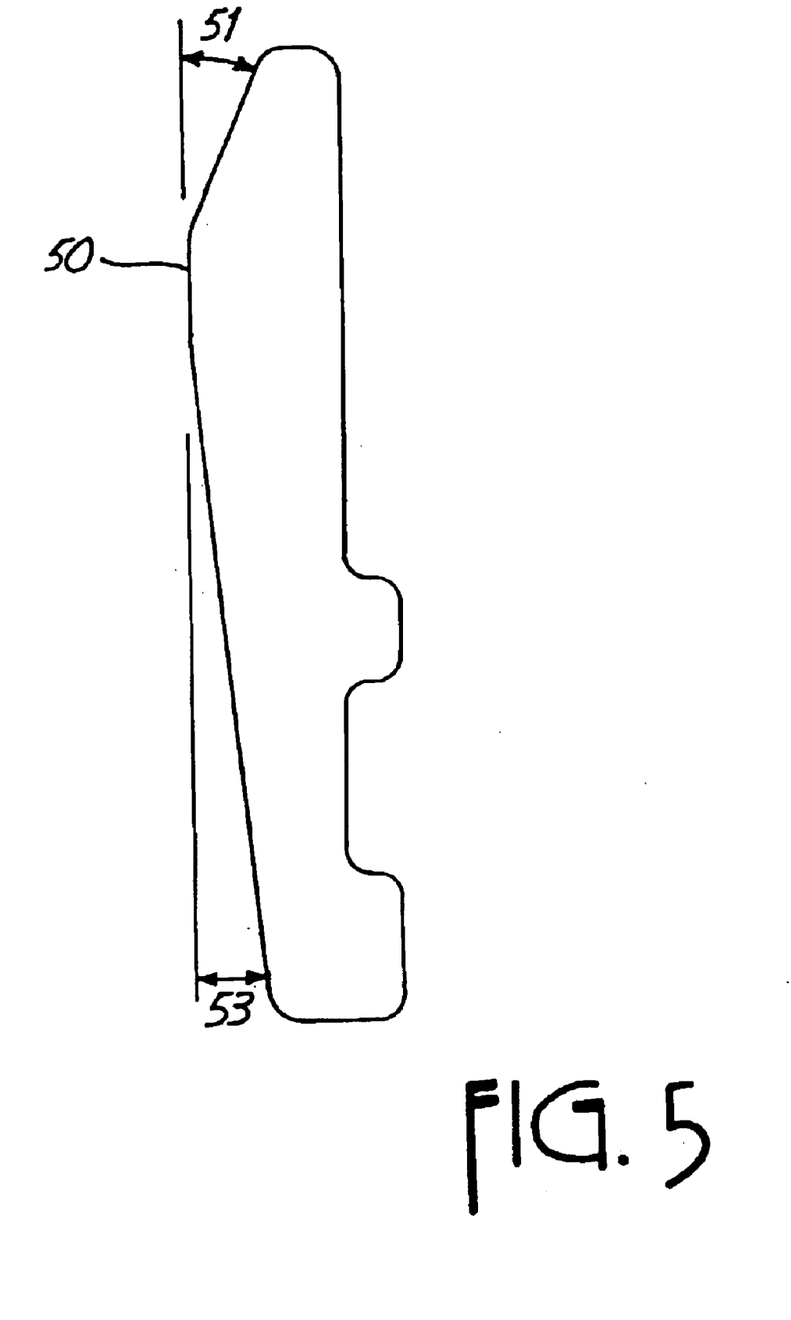
FIG. 5 is a side cross-sectional view of the prosthetic heart valve of FIG. 3.

As the spacing of the axes of the minor radius diameter arcs 24 is altered, the angle 51,53 of the tapered sections 70,72 should also change appropriately, but will generally fall within a range of about 0 to 45° as illustrated in FIG. 5. In the case where the radii 30 and 32 are the same (FIG. 8A), the angles 51,53 of the tapered sections 70 and 72 is zero and the tapered surfaces are eliminated. The length of peak extension 50 in FIG. 3, formed between the inflow and outflow tapers 70 and 72, provides a sealing surface for the occluders 40 and 42 when in the closed position.

Figure 4:
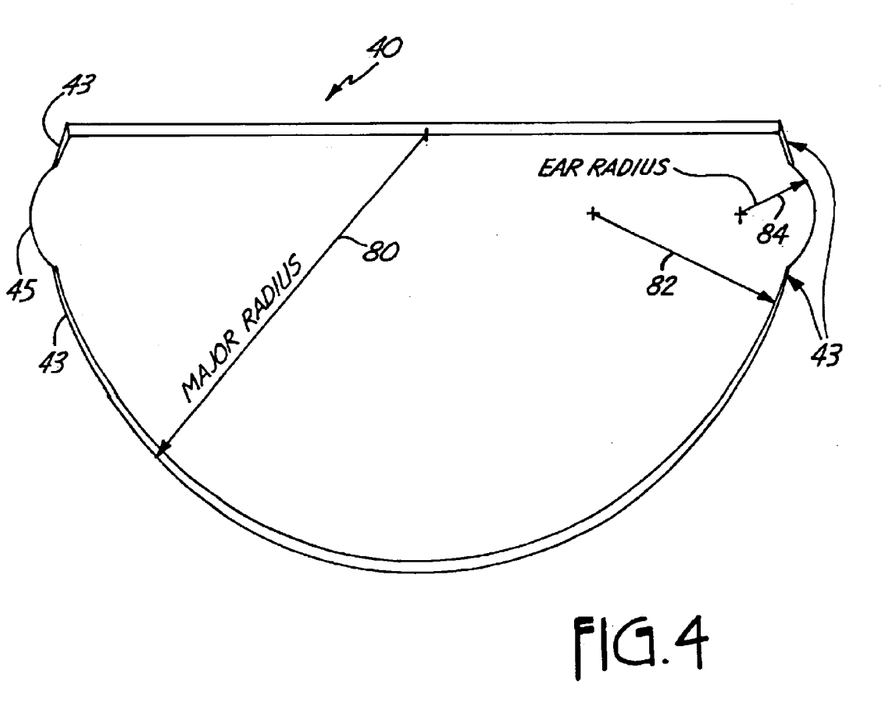
FIG. 4 is a side plan view of an occluder in accordance with the present invention.

FIG. 4 is a side plan view of an occluder 40. FIG. 4 illustrates the major radius 80 of occluder 40 and the minor radius 82 which forms minor radius arcs 43 configured to mate with the minor radius arcs 24 of the valve body to form a seal in the closed position. FIG. 4 also illustrates the ear radius 84 which is configured to mate with pivot mechanism 60.

Figure 6:
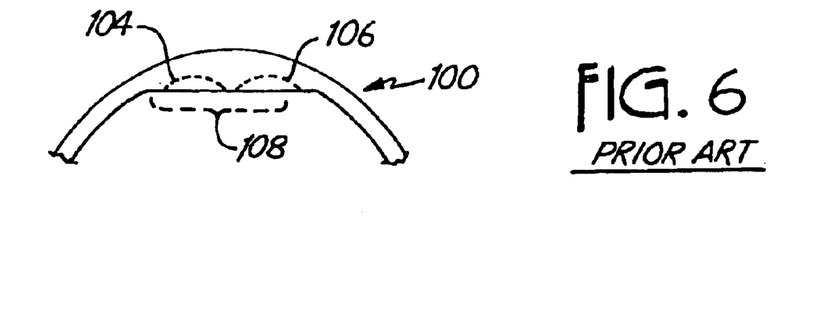
FIG. 6 is a plan view of a portion of a prior art valve body.

For comparison, FIG. 6 shows a partial plan view of a prior art valve body 100 where pivot mechanisms 104 and 106 are formed in valve body 100. As illustrated in FIG. 6, valve body 100 includes a substantially flat face 108 which tends to reduce the area of the lumen through body 100.

FIGS. 7A, 8A, 9A and 10A show various example embodiments of the present invention and illustrate the increase in lumen area in comparison to the prior art design of FIG. 6. In FIG. 7A, 8A, 9A and 10A, the flat face 108 of FIG. 6 is illustrated with a dashed line.

Figure 7A:
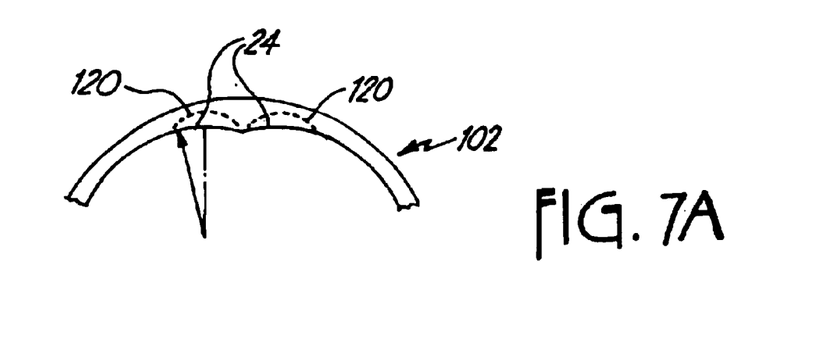
FIGS. 7A, 8A, 9A and 10A are plan views of portions of valve bodies in accordance with various embodiments of the invention.
Figure 7B:
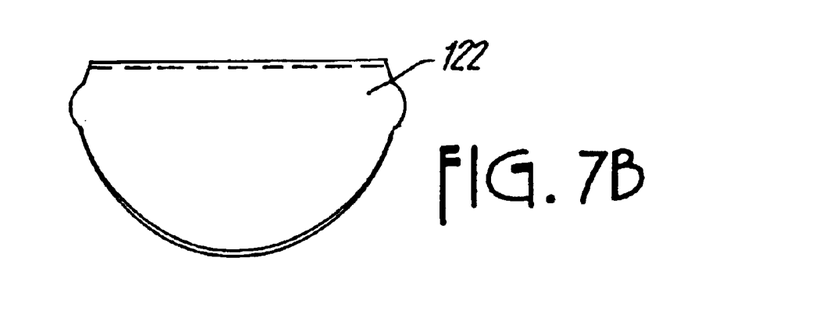
FIGS. 7B, 8B, 9B and 10B are plan views of occluders for use with the valve body shown in FIGS. 7A, 8A, 9A and 10A, respectively.

FIG. 7A shows an example embodiment of the present invention in which the pivot mechanisms 120 are moved outward in comparison to FIG. 6 and minor arcs are added. In FIG. 7A, the pivot mechanisms 120 lie completely on the minor radius arcs 24. The minor arcs provide improved leaflet/occluder retention. FIG. 7B shows a corresponding occluder 122 for use with valve body 102 of FIG. 7A.

Figure 8A:
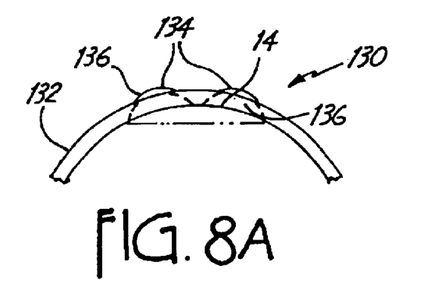
Figure 8B:
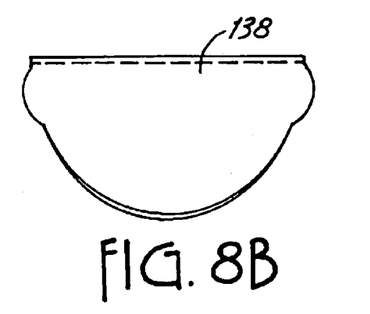

In FIG. 8A, an embodiment of valve body 130 is shown in which the outer circumference 132 of the body includes protrusions 134 to provide additional room for pivot mechanism 136. The pivot mechanisms 136 lie completely on the cylindrical inner wall diameter 14. This configuration has the largest lumen area, and the least resistance to flow through the valve. A corresponding occluder 138 is shown in FIG. 8B for use with valve body 130.

Figure 9A:
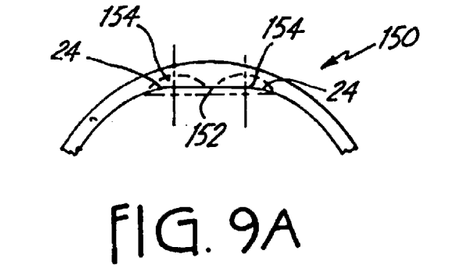
Figure 9B:
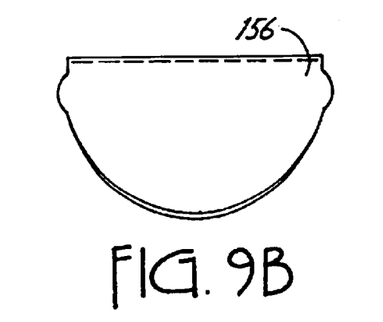

In FIG. 9A, an embodiment of valve body 150 is shown in which a small flat region 152 is positioned between center lines of pivot mechanism 154. The pivot mechanisms 154 lie partially on the flat region 152 and partially on the curved minor radius arcs 24. The peak extension 50 is generally eliminated so that the lumen area is increased. FIG. 9B shows an occluder 156 for use with the valve body 150 in FIG. 9A.

Figure 10A:
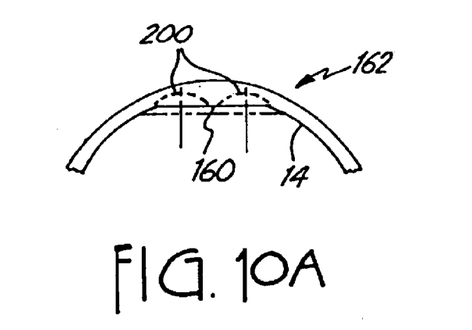
Figure 10B:
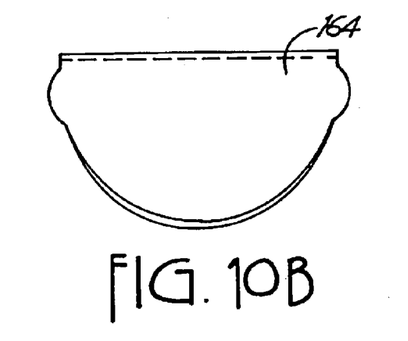

FIG. 10A shows another example embodiment in which a flat portion 160 of valve body 162 is extended to the major arc of the valve body. The corresponding occluder 164 is shown in FIG. 10B. The pivot mechanisms 200 lie partially on the flat portion 160 and partially on the inner wall diameter 14. This configuration does not have minor radius arcs.

With the present invention, the lumen area through the valve is increased from 3% to up to more than 23% in some configurations. The valve of the present invention can be fabricated using any technique or material. However, pyrolytic carbon or other biocompatible materials such as titanium, materials coated with diamond-like carbon, or other materials are preferred, including rigid polymers or reinforced polymers. The present invention can be applied to any valve configuration including tri-leaflet or central opening valve designs.

The present invention provides a number of advantages over prior art configurations. In-vitro test results show that the present invention provides improved hydrodynamic flow in comparison to traditional mechanical heart valve prosthesis designs. Measurements in an in-vitro steady forward flow test setup show a lower pressure drop across a prototype of the current invention compared to industry leading bi-leaflet design as follows:

Decrease in pressure differential across valve at physiologic flow rates of valve illustrated in FIGS. 3 and 7 as compared to a valve in FIG. 6.

| Flow Rate | Decrease in Δp |
| --- | --- |
| 20 LPM | 17% |
| 25 LPM | 25% |
| 30 LPM | 25% |

Valves can be characterized using a number of measurement techniques. Traditional measurements of valve efficiency include measuring the pressure differential across the valve at physiologic peak forward flow rates. Additional flow characterization can be made by flow visualization techniques or velocity profile mapping techniques such as laser doppler velocimetry (LDV) or digital particle image velocimetry (DPIV). Velocity mapping techniques can also be used to calculate the shear stresses in the flow, as well as provide an overall view of the divergence or turbulence present in the flow.

Figure 11:
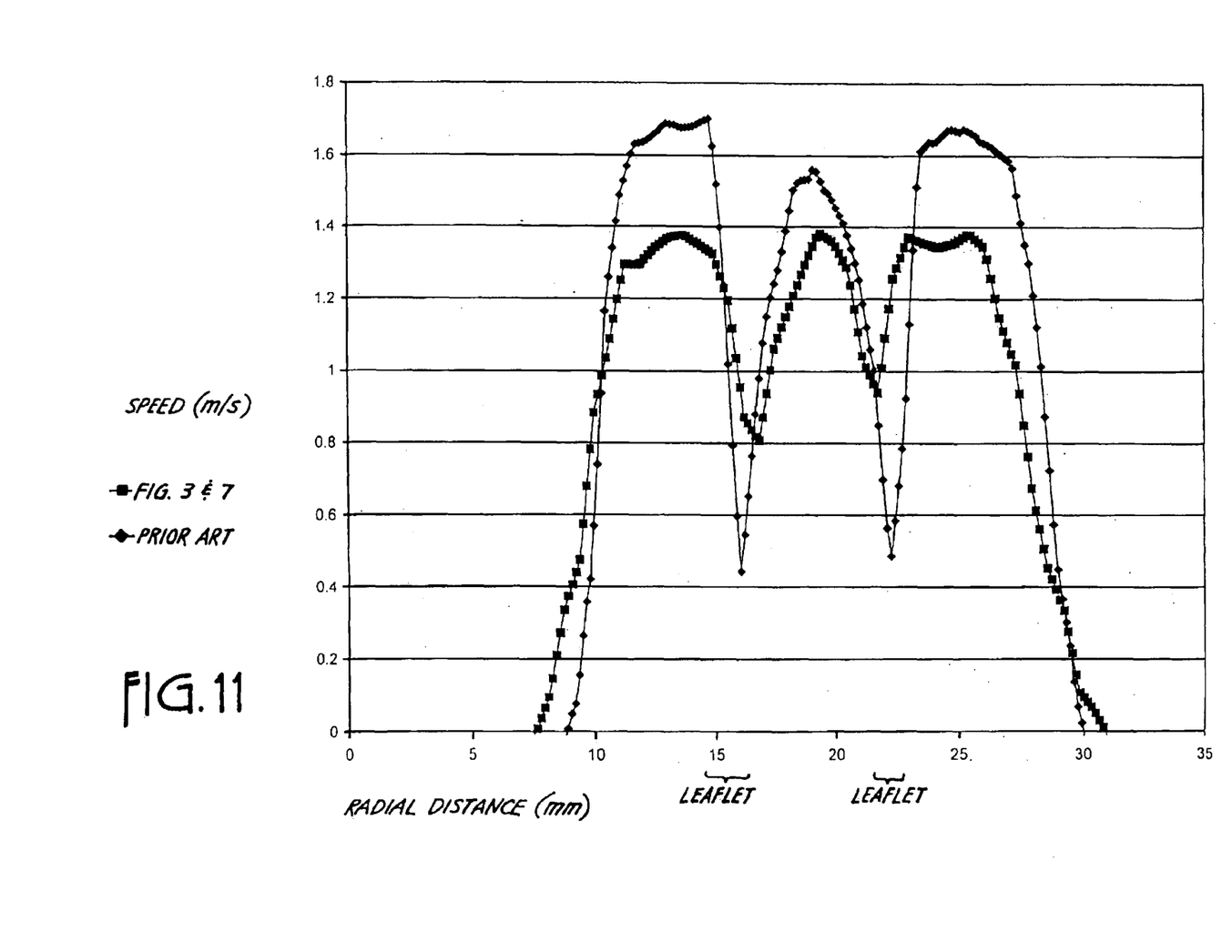
FIG. 11 is a graph of velocity profiles of a prior art heart valve and a heart valve in accordance with the embodiment shown in FIGS. 3 and 7.

FIG. 11 is a graph of velocity profiles for a prior art valve and a valve in accordance with the embodiment of FIGS. 3 and 7. The profile is taken at a plane 4 mm downstream from the valve using the DPIV technique. The velocity profiles in FIG. 11 show that there is slower forward flow velocity for the present invention (approximately 30 cm/s slower peak velocity) as well as more even flow distribution across the flow profile than typical prior art designs. The increased lumen area of the present invention and the full 90 degree opening in the leaflets produces the slower, more uniform velocity distribution. The more even flow distribution across the valve produces lower shear stresses than prior art valves.

The reduced velocity and reduced shear stresses of the improved valve is expected to cause less damage to red blood cells or platelets passing through the valve. Traditional gross measurements of hemodynamic performance (i.e., pressure drop across valve) show an improvement of about 20% over typical mechanical heart valves. However, more sensitive measures of blood damage and platelet activation may show enhanced improvement as well, due to the more laminar flow and reduced velocity gradients in the flow profile of the improved valve.

The present invention provides designs to increase the orifice lumen and streamline the lumen shape in a prosthetic mechanical heart valve. The increased lumen provides improved blood flow with less restriction. Further, the increased opening is achieved without increasing the overall size of the prosthetic heart valve or requiring significant manufacturing changes.

Although the present invention has been described with reference to preferred embodiments, workers skilled in the art will recognize that changes may be made in form and detail without departing from the spirit and scope of the invention. For example, the invention can be applied to any heart valve configuration which uses an occluder including two piece valves. Further, the valve can be attached to the native tissue using any technique.

What is claimed is:

1. A prosthetic heart valve for replacing a native valve in a heart, comprising:
   a generally circular heart valve body having an interior wall defining a lumen configured to allow blood flow therethrough;
   at least one occluder in the lumen comprising first and second minor radius arcs defined by respective minor radii, and at least one major radius arc disposed between the first and second minor radius arcs and defined by a major radius greater than the minor radii; and
   an occluder rotation mechanism having first and second elements disposed at the occluder in proximity to the first and second minor radius arcs respectively, and third and fourth elements disposed at the interior wall of the heart valve body, the first and second elements being respectively in engagement with the third and fourth elements for enabling rotation of the occluder about an axis thereof between an open position and a closed position relative to the interior wall of the heart valve body;
   wherein the interior wall of the heart valve body comprises minor radius arcs proximate the first and second elements of the occluder rotation mechanism to receive the minor radius arcs of the occluder in the closed position, the minor radius arcs of the heart valve body having curved surfaces.

2. The prosthetic heart valve of claim 1 including respective inflow tapers proximate the minor radius arcs of the interior wall of the heart valve body.

3. The prosthetic heart valve of claim 1 including respective outflow tapers proximate the minor radius arcs of the interior wall of the heart valve body.

4. The prosthetic heart valve of claim 1 wherein the minor radius arcs of the interior wall of the heart valve body are substantially tangent to a major radius arc of the lumen of the heart valve body.

5. The prosthetic heart valve of claim 4 wherein a length of a radius of the major radius arc of the lumen of the heart valve body is approximately twice a length of radii of the minor radius arcs of the interior wall of the heart valve body.

6. The prosthetic heart valve of claim 4 wherein spacing between axes of the minor radius arcs of the interior wall of the heart valve body is approximately 15–25% of a diameter of the lumen.

7. The prosthetic heart valve of claim 2 wherein the minor radius arcs of the interior wall of the heart valve body are substantially tangent to a major radius arc of the lumen of the heart valve body.

8. The prosthetic heart valve of claim 3 wherein the minor radius arcs of the interior wall of the heart valve body are substantially tangent to a major radius arc of the lumen of the heart valve body.

9. The prosthetic heart valve of claim 1 including peak extensions proximate the minor radius arcs of the interior wall of the heart valve body.

10. The prosthetic heart valve of claim 1 wherein the third and fourth elements comprise pivot mechanisms formed in the interior wall and carried on the curved surface of the interior wall.

11. The prosthetic heart valve of claim 10 wherein the curved surface is formed by the minor radius arcs of the interior wall of the heart valve body.

12. The prosthetic heart valve of claim 1 wherein the minor radius arcs of the at least one occluder mate with the minor radius arcs of the heart valve body.

13. The prosthetic heart valve of claim 1 wherein a center of the minor radius arcs of the interior wall of the heart valve body are coincident with the occluder axis.

14. The prosthetic heart valve of claim 1 including a flat portion positioned between curved surfaces of the minor radius arcs of the heart valve body.

15. A prosthetic heart valve for replacing a native valve in a heart, comprising:
   a generally circular heart valve body having an interior wall defining a lumen configured to allow blood flow therethrough;
   at least one occluder in the lumen including opposed occluder ends and configured to rotate about the opposed occluder ends between an open position and a closed position, the occluder including minor radius arcs disposed proximate the occluder ends;

opposed pivots on an interior wall of the heart valve body configured to receive the opposed occluder ends; and minor radius arcs formed in the interior wall of the heart valve body proximate the opposed pivots to receive the minor radius arcs of the occluder, the minor radius arcs of the heart valve body having curved surfaces;

wherein the minor radius arcs formed in the interior wall of the heart valve body are substantially tangent to a major radius arc of the lumen of the heart valve body; and wherein a length of a radius of the major radius arc is approximately twice a length of the radii of minor radius arcs.

16. A prosthetic heart valve for replacing a native valve in a heart, composing:

a generally circular heart valve body having an interior wall defining a lumen configured to allow blood flow therethrough;

at least one occluder in the lumen including opposed occluder ends and configured to rotate about the opposed occluder ends between an open position and a closed position, the occluder including minor radius arcs disposed proximate the occluder ends;

opposed pivots on an interior wall of the heart valve body configured to receive the opposed occluder ends; and minor radius arcs formed in the interior wall of the heart valve body proximate the opposed pivots to receive the minor radius arcs of the occluder, the minor radius arcs of the heart valve body having curved surfaces;

wherein the minor radius arcs formed in the interior wall of the heart valve body are substantially tangent to a major radius arc of the lumen of the heart valve body; and wherein spacing between axes of the minor radius arcs formed in the interior wall of the heart valve body is approximately 15–25% of a diameter of the lumen.

17. A prosthetic heart valve for replacing a native valve in a heart, comprising:

a generally circular heart valve body having an interior wall defining a lumen configured to allow blood flow therethrough;

at least one occluder in the lumen including opposed occluder ends and configured to rotate about the opposed occluder ends between an open position and a closed position, the occluder including minor radius arcs disposed proximate the occluder ends;

opposed pivots on an interior wall of the heart valve body configured to receive the opposed occluder ends;

minor radius arcs formed in the interior wall of the heart valve body proximate the opposed pivots to receive the minor radius arcs of the occluder, the minor radius arcs of the heart valve body having curved surfaces; and an inflow taper proximate the minor radius arcs of the heart valve body.

18. A prosthetic heart valve for replacing a native valve in a heart, comprising:

a generally circular heart valve body having an interior wall defining a lumen configured to allow blood flow therethrough;

at least one occluder in the lumen including opposed occluder ends and configured to rotate about the opposed occluder ends between an open position and a closed position, the occluder including minor radius arcs disposed proximate the occluder ends;

opposed pivots on an interior wall of the heart valve body configured to receive the opposed occluder ends;

minor radius arcs formed in the interior wall of the heart valve body proximate the opposed pivots to receive the minor radius arcs of the occluder, the minor radius arcs of the heart valve body having curved surfaces; and an outflow taper proximate the minor radius arcs of the heart valve body.

\* \* \* \* \*